United States Patent
Funakoshi et al.

(10) Patent No.: US 9,778,208 B2
(45) Date of Patent: Oct. 3, 2017

(54) OPERATION DEVICE FOR INTO-BORE INTRODUCTION DEVICE, AND INTO-BORE INTRODUCTION DEVICE

(71) Applicant: OLYMPUS CORPORATION, Hachioji-shi, Tokyo (JP)

(72) Inventors: Yasuo Funakoshi, Hachioji (JP); Kenji Tajima, Hachioji (JP); Yuki Hoshino, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/132,658

(22) Filed: Apr. 19, 2016

(65) Prior Publication Data
US 2016/0231255 A1    Aug. 11, 2016

Related U.S. Application Data

(63) Continuation of application No. PCT/JP2014/082318, filed on Dec. 5, 2014.

(30) Foreign Application Priority Data

Dec. 13, 2013 (JP) ................................ 2013-258454

(51) Int. Cl.
*A61B 1/04*    (2006.01)
*G01N 21/954*    (2006.01)
(Continued)

(52) U.S. Cl.
CPC ......... *G01N 21/954* (2013.01); *A61B 1/0052* (2013.01); *A61B 1/00071* (2013.01);
(Continued)

(58) Field of Classification Search
CPC ........................ A61B 1/00066; A61B 1/00068
(Continued)

(56) References Cited

U.S. PATENT DOCUMENTS 4,566,437 A * 1/1986 Yamaguchi .......... A61B 1/0055
600/131
4,616,630 A * 10/1986 Arakawa .............. A61B 1/0052
600/131
(Continued)

FOREIGN PATENT DOCUMENTS

EP    2835096 A1    2/2015
JP    S63-84116 U    6/1988
(Continued)

OTHER PUBLICATIONS

Mar. 3, 2015 International Search Report issued in International Patent Application No. PCT/JP2014/082318.
(Continued)

*Primary Examiner* — Matthew J Kastejna
(74) *Attorney, Agent, or Firm* — Oliff PLC (57) ABSTRACT

An operation device for an into-bore introduction device, includes: a grasping section connected to a proximal portion of an insertion section to be inserted into a bore, and is to be grasped by an operator to operate the insertion section; a bending operation knob disposed on the grasping section and bends a bending portion of the insertion section; a projecting portion formed to project from the grasping section in a direction radial to a longitudinal axis of the grasping section, in a surface between a surface on which the bending operation knob is disposed and a surface on which operator's palm abuts to grasp the grasping section, in the grasping section; and an inclined surface inclined toward the insertion section on an insertion section side of the projecting portion.

7 Claims, 6 Drawing Sheets

(51) Int. Cl.
  *G02B 23/24* (2006.01)
  *A61B 1/005* (2006.01)
  *A61B 1/00* (2006.01)
  *G05G 1/10* (2006.01)
  *G05G 11/00* (2006.01)

(52) U.S. Cl.
  CPC ...... *A61B 1/00133* (2013.01); *G02B 23/2476* (2013.01); *G05G 1/10* (2013.01); *G05G 11/00* (2013.01); *G01N 2021/9542* (2013.01)

(58) Field of Classification Search
  USPC ........................................................ 600/131
  See application file for complete search history.

(56) References Cited

U.S. PATENT DOCUMENTS

| | | | | |
|---|---|---|---|---|
| 5,447,148 | A * | 9/1995 | Oneda | A61B 1/00091 600/131 |
| 6,520,908 | B1 * | 2/2003 | Ikeda | A61B 1/00121 600/110 |
| 8,092,373 | B1 * | 1/2012 | Papouras | A61B 1/00066 600/102 |
| 8,118,732 | B2 * | 2/2012 | Banik | A61B 1/00059 600/117 |
| 8,858,427 | B2 * | 10/2014 | Yamazaki | A61B 1/00066 600/104 |
| 2004/0082835 | A1 * | 4/2004 | Ishizuka | A61B 1/00068 600/133 |
| 2004/0176660 | A1 * | 9/2004 | Abe | A61B 1/00059 600/101 |
| 2007/0249904 | A1 * | 10/2007 | Amano | A61B 1/00052 600/131 |
| 2008/0086031 | A1 | 4/2008 | Mitsuya | |
| 2012/0165605 | A1 * | 6/2012 | Yamazaki | A61B 1/00066 600/106 |
| 2013/0012780 | A1 * | 1/2013 | Nakamura | A61B 1/0052 600/122 |
| 2014/0100424 | A1 * | 4/2014 | Hoshino | H01H 13/14 600/118 |
| 2014/0187864 | A1 * | 7/2014 | Kubo | A61B 1/00066 600/139 |
| 2014/0200513 | A1 * | 7/2014 | Koitabashi | A61B 1/00066 604/95.04 |
| 2015/0025319 | A1 | 1/2015 | Koyama | |
| 2015/0057537 | A1 * | 2/2015 | Dillon | A61B 1/0014 600/431 |
| 2016/0242629 | A1 * | 8/2016 | Hijihara | A61B 1/0052 |

FOREIGN PATENT DOCUMENTS

| | | |
|---|---|---|
| JP | H06-142030 A | 5/1994 |
| JP | 2004-141331 A | 5/2004 |
| JP | 2008-092968 A | 4/2008 |

OTHER PUBLICATIONS

Jun. 23, 2016 International Preliminary Report on Patentability issued in International Application No. PCT/JP2014/0823113.
Aug. 3, 2017 Search Report issued in European Patent Application No. 14869725.3.

\* cited by examiner

OPERATION DEVICE FOR INTO-BORE INTRODUCTION DEVICE, AND INTO-BORE INTRODUCTION DEVICE

CROSS-REFERENCE TO RELATED APPLICATIONS

This application is a Continuation Application of PCT Application No. PCT/JP2014/082318, filed Dec. 5, 2014 and based upon and claiming the benefit of priority from prior Japanese Patent Application No. 2013-258454, filed Dec. 13, 2013, the entire contents of all of which are incorporated herein by reference.

BACKGROUND OF THE INVENTION

1. Field of the Invention

This invention relates to an operation device for an into-bore introduction device to introduce an insertion section into a bore, and the into-bore introduction device.

2. Description of the Related Art

In an operation device for an into-bore introduction device (an operation device of an endoscope) which is disclosed in, for example, Jpn. Pat. Appln. KOKAI Publication No. 2004-141331 and Jpn. Pat. Appln. KOKAI Publication No. 2008-92968, there is a stepped portion between a first grasping portion and a second grasping portion. The operation device is grasped in a stabilized state by placing a middle finger and a ring finger on a lower side of the stepped portion.

BRIEF SUMMARY OF THE INVENTION

According to one embodiment of the present invention, an operation device for an into-bore introduction device, includes: a grasping section that is connected to a proximal portion of an insertion section to be inserted into a bore, and is to be grasped by an operator to operate the insertion section; a bending operation knob that is disposed on the grasping section and that bends a bending portion of the insertion section; a projecting portion that is formed to project from the grasping section in a direction radial to a longitudinal axis of the grasping section, in a surface between a surface on which the bending operation knob is disposed and a surface on which operator's palm abuts to grasp the grasping section, in the grasping section; and an inclined surface that is inclined toward the insertion section on an insertion section side of the projecting portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

A first embodiment will be described with reference to FIG. 1 to FIG. 4B.

Figure 1:
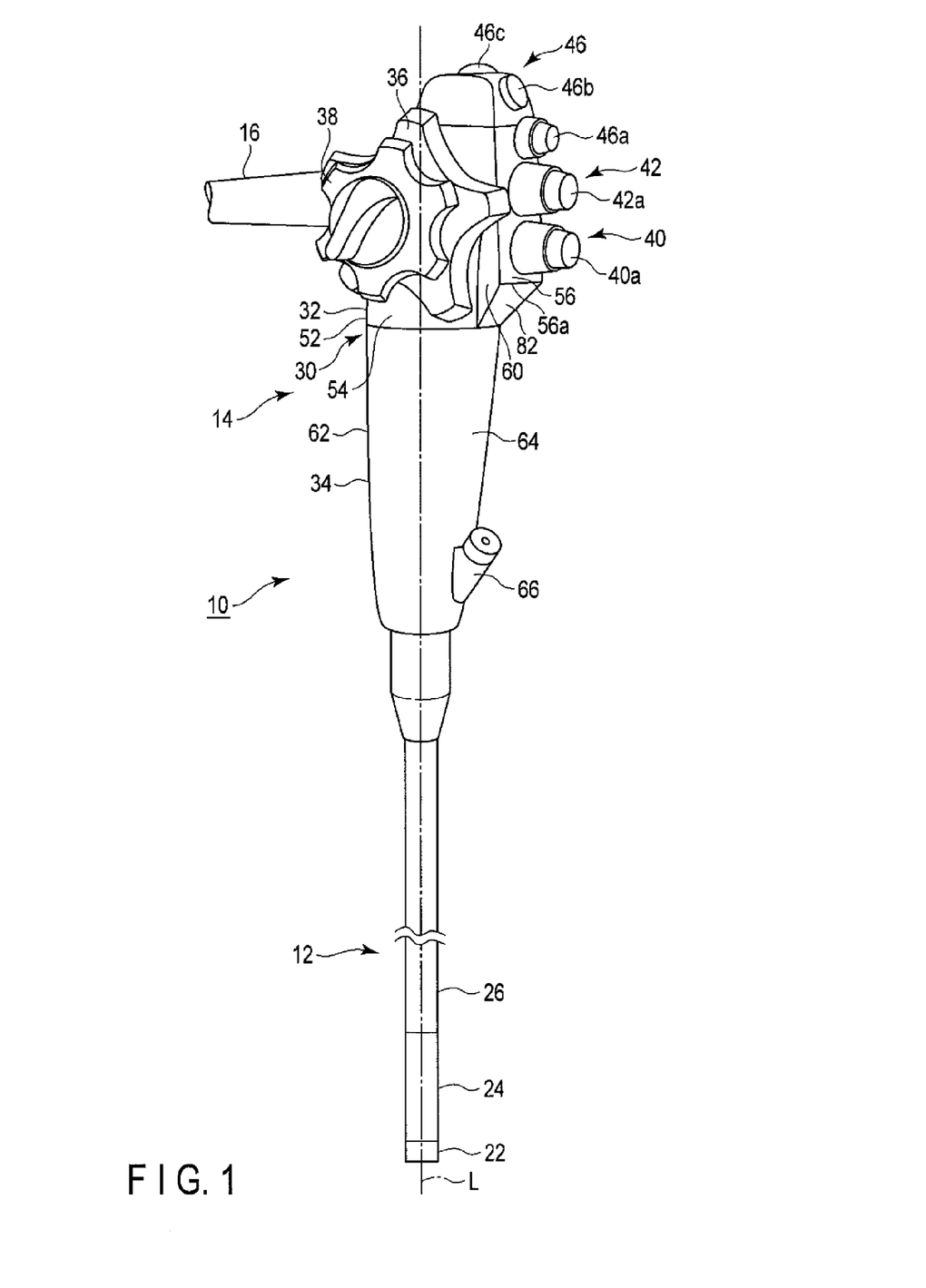
FIG. 1 is a schematic view showing an endoscope (an into-bore introduction device) according to first to third embodiments.
Figure 2A:
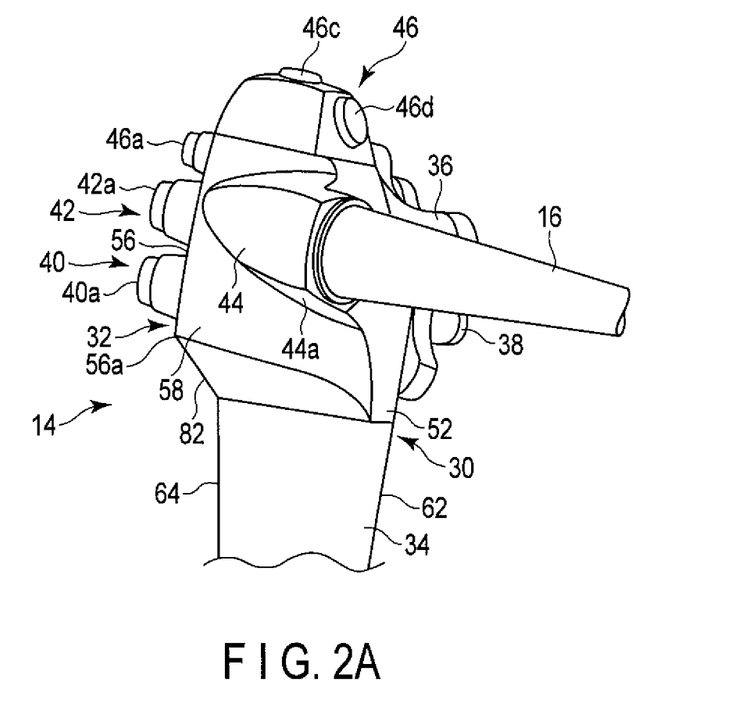
FIG. 2A is a schematic view showing an operation device of the endoscope (the into-bore introduction device) according to the first to third embodiments, and showing a state shown in FIG. 1 seen from an opposite side.
Figure 2B:
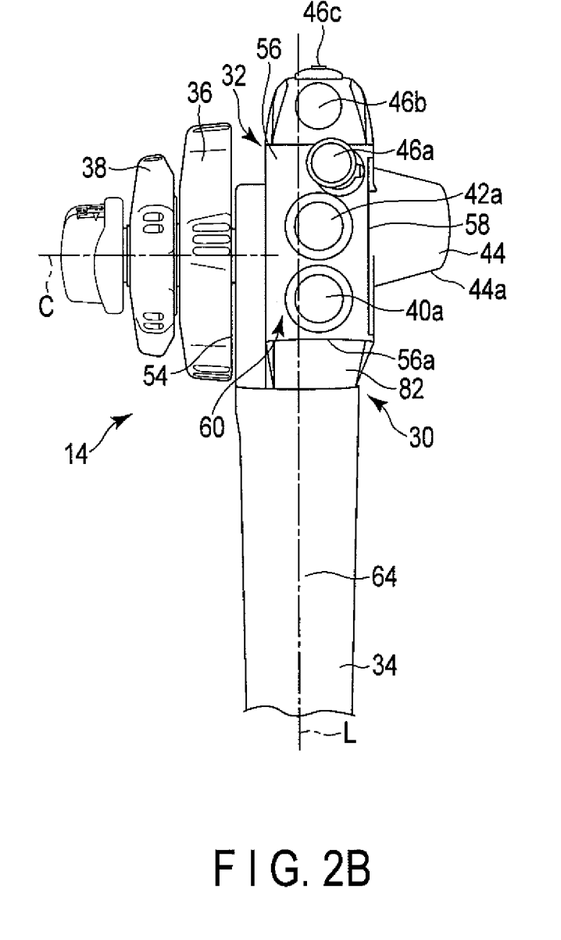
FIG. 2B is a schematic view showing the operation device of the endoscope (the into-bore introduction device) according to the first to third embodiments.

As shown in FIG. 1, in this embodiment, an endoscope 10 will be described as an example of an into-bore introduction device.

The endoscope (the into-bore introduction device) 10 includes an insertion section 12 to be inserted into a bore, an operation device 14 to be grasped with one of a user's hands, especially the left hand for use in suitably operating the endoscope 10 including the insertion section 12, and a universal cord 16 to be connected to an unshown control unit that controls the endoscope 10.

Although not shown in the drawing, the endoscope 10 includes therein a known illumination optical system that illuminates the inside of the bore, and a known observation optical system in which the inside of the bore illuminated with the illumination optical system is imaged and observed. The endoscope 10 further includes a known air supply/water supply/suction unit capable of washing an unshown objective lens and the like of the observation optical system and sucking a biological tissue, blood and the like.

The insertion section 12 includes a distal hard portion 22, a bending portion 24, and a tubular member 26 having a flexibility in order from a distal portion to a proximal portion of the insertion section 12. As the tubular member 26, a member having the flexibility, e.g., a flexible tube of an insertion section of a so-called flexible endoscope is preferably used, but a hard tube that is made of a metal material such as a stainless alloy material and does not have the flexibility may be used.

The operation device 14 is disposed in the proximal portion of the insertion section 12. The insertion section 12 and the operation device 14 are present on a common longitudinal axis L. Specifically, the insertion section 12 is coupled with a second grasping portion 34 that will be described later, and extended to a side opposite to a first grasping portion 32.

As shown in FIG. 1 to FIG. 4B, the operation device 14 includes a grasping section 30 to be grasped by an operator to operate the insertion section 12, a UD bending operation knob 36, an RL bending operation knob 38, pressing valve units (here, first and second pressing valve units) 40 and 42, and a connector 44 from which the universal cord 16 is extended outside. The grasping section 30 includes a first grasping portion (an upper grasping portion) 32 and a second grasping portion (a lower grasping portion) 34.

The longitudinal axis L of the insertion section 12 is present on a central axis of the insertion section 12. The second grasping portion 34 of the operation device 14 is positioned closer to the insertion section 12 than the first grasping portion 32 along the longitudinal axis L.

The first pressing valve unit 40 is present on a side (a lower side) close to the second grasping portion 34 and the insertion section 12, and is used to perform air supply or water supply to discharge a gas or a liquid from a distal end of the distal hard portion 22 of the insertion section 12. The second pressing valve unit 42 is present on a side (an upper side) away from the insertion section 12, and is used to suck a biological tissue, blood or the like present at the distal end of the distal hard portion 22 of the insertion section 12. The first and second pressing valve units 40 and 42 are parts of the abovementioned known air supply/water supply/suction unit inserted from a distal end of the insertion section 12 of the endoscope 10 into a distant end of the universal cord 16 from the operation device 14. It is to be noted that the first and second pressing valve units 40 and 42 according to this embodiment preferably have the same size and the same appearance in shape.

Additionally, on the upper side of the second pressing valve unit 42 in the first grasping portion 32, a switch unit 46 having switches 46a, 46b, . . . is disposed. Functions of the switches 46a, 46b, . . . are suitably set. One of the switches of the switch unit 46 has, for example, a function set by the unshown control unit of the endoscope 10 and used to image a static image. Additionally, one of the other switches has, for example, a function set by the unshown control unit and used to switch illumination light to usual light (incandescent light) or special light (e.g., fluorescent light).

The first grasping portion 32 includes, as an outer peripheral surface, a first surface (a user facing surface) 52, a second surface (an operation knob disposing face) 54, a third surface (a pressing valve unit disposing face) 56 and a fourth surface (a universal cord disposing face) 58 in a peripheral direction around the longitudinal axis L. A boundary between the first surface 52 and the second surface 54, a boundary between the second surface 54 and the third surface 56, a boundary between the third surface 56 and the fourth surface 58 and a boundary between the fourth surface 58 and the first surface 52 are formed into smoothly curved surfaces via each of which both the faces are continuous with each other. The outer peripheral surface of the first grasping portion 32 along the peripheral direction around the longitudinal axis L is formed into an annular shape in which the first to fourth surfaces 52, 54, 56 and 58 cooperate. The outer peripheral surface of the first grasping portion 32, i.e., a shell is preferably formed into, for example, a tubular shape having a substantially rectangular transverse cross section.

The second grasping portion 34 includes, as an outer peripheral surface, a user facing surface (a fifth surface) 62 continuous with the first surface 52, and a grip face (a sixth surface) 64 in the peripheral direction around the longitudinal axis L. A transverse cross section of the grip face 64 which is orthogonal to the longitudinal axis L is formed into a substantially U-shape. That is, the outer peripheral surface of the second grasping portion 34 in the peripheral direction orthogonal to the longitudinal axis L is formed into an annular shape in which the fifth and sixth surfaces 62 and 64 cooperate. It is to be noted that at a position of the grip face 64 which is close to the insertion section 12, there is formed a treatment device inlet 66 (see FIG. 1) to project a treatment device from, for example, a distal face of the distal hard portion 22 through an unshown channel.

When the first and second grasping portions 32 and 34 of the endoscope 10 are grasped with one hand (the left hand), the first surface 52 and the user facing surface 62 can face the user. In a state where the first surface 52 and the user facing surface 62 face the user, the second surface 54 of the first grasping portion 32 is formed as a right side face disposed on the first surface 52, on the user's right side, and the fourth surface 58 is formed as a left side face disposed on the first surface 52, on the user's left side. It is to be noted that the third surface 56 of the first grasping portion 32 is present on a surface (a back surface) opposite to the first surface 52, and is continuous with the second surface 54 and the fourth surface 58. It is to be noted that the third surface 56 is present on the side of the sixth surface 64 of the second grasping portion 34 which is opposite to the fifth surface 62, and is positioned to project out from the sixth surface 64 in a direction radial to the longitudinal axis L. Consequently, not only the third surface 56 but also parts of the second surface 54 and the fourth surface 58 form a projecting portion 60 that projects out from the sixth surface 64 in the direction radial to the longitudinal axis L. That is, the projecting portion 60 is disposed on the third surface 56 formed between the second surface 54 on which the UD bending operation knob 36 is disposed and the fourth surface 58 on which an operator's palm abuts to grasp the first grasping portion 32.

On the second surface 54 of the first grasping portion 32, the UD bending operation knob 36 is turnably and operably disposed. That is, the UD bending operation knob 36 is disposed on the second surface 54 of the first grasping portion 32 which is opposite to the fourth surface 58 adjacent to the first surface 52 in the peripheral direction, and operated by the user when the bending portion 24 of the insertion section 12 is bent. The UD bending operation knob 36 is formed into a substantially star shape having five convex portions 72 whose outer edges come in contact with an outer peripheral surface of a virtual circle based on a rotation central axis C of the UD bending operation knob 36, and five concave portions 74 formed between the respective convex portions 72 and concaved to the circle on the side of the rotation central axis C of the UD bending operation knob 36. It is to be noted that a central axis of the UD bending operation knob 36 matches the rotation central axis C.

On the third surface 56, the first and second pressing valve units 40 and 42 are disposed. That is, the first and second pressing valve units 40 and 42 are disposed on the third surface 56 of the first grasping portion 32 which is adjacent to the second surface 54 in the peripheral direction and opposite to the first surface 52. The first pressing valve unit 40 is present in the third surface 56, i.e., the projecting portion 60, and is therefore positioned more distant from the longitudinal axis L than the sixth surface 64 at the position close to at least the second grasping portion 34.

On the fourth surface 58, the connector 44 for the universal cord is disposed. The universal cord 16 is extended from the connector 44 toward the user. That is, the universal cord 16 is extended toward a side opposite to the third surface 56. A lower surface 44a of the connector 44 is formed as a support portion on which the user's index finger or the like is placed and supported, when the user grasps the operation device 14.

Figure 3:
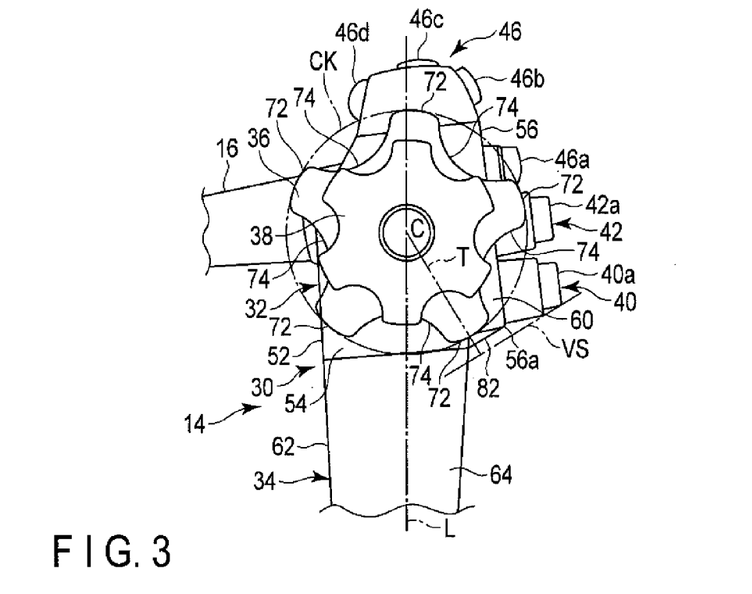
FIG. 3 is a schematic front view showing the operation device of the endoscope (the into-bore introduction device) according to the first embodiment.
Figure 4A:
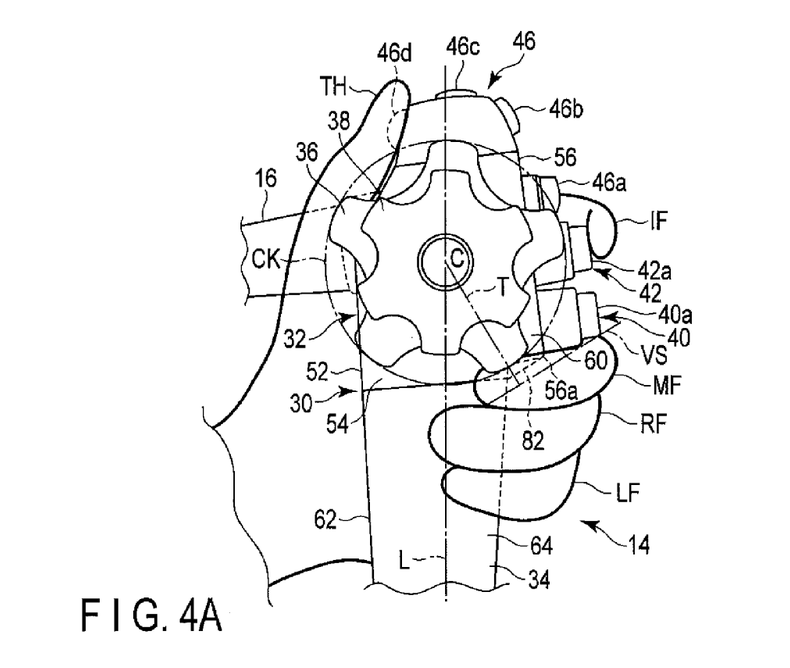
FIG. 4A is a schematic view showing a state where the operation device of the endoscope (the into-bore introduction device) according to the first embodiment is grasped with a left hand, especially a middle finger is placed on an inclined surface, and a ring finger and a little finger are placed on a grip face of the second grasping portion.
Figure 4B:
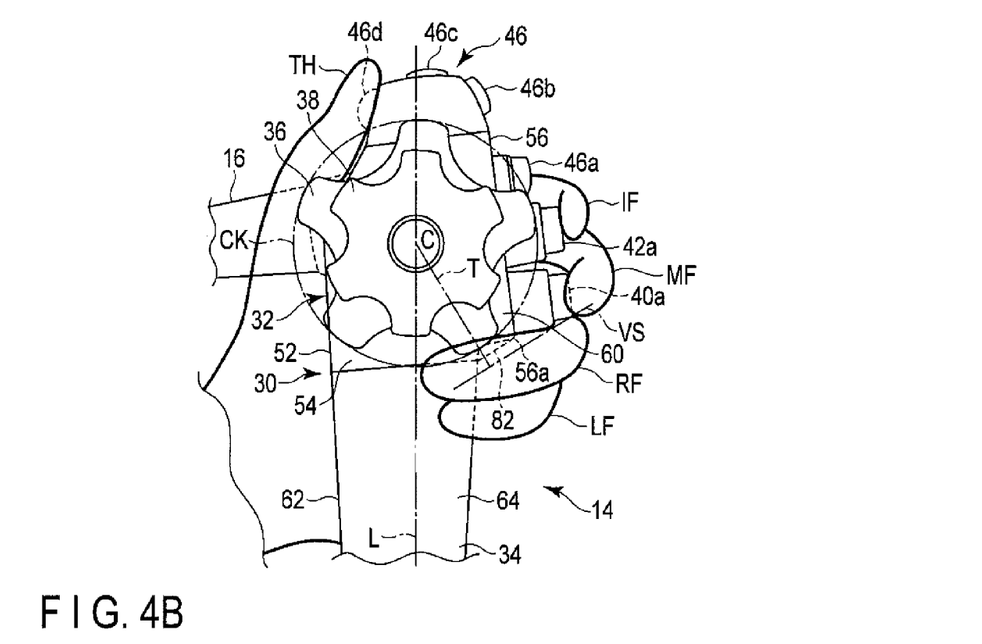
FIG. 4B is a schematic view showing a state where the operation device of the endoscope (the into-bore introduction device) according to the first embodiment is grasped with the left hand, especially the middle finger is placed on a pressing member of a first pressing valve unit, the ring finger is placed on the inclined surface, a UD bending operation knob is supported with the ring finger, and the little finger is placed on the grip face of the second grasping portion.

It is to be noted that a boundary between the first surface 52 of the first grasping portion 32 and the user facing surface (the fifth surface) 62 of the second grasping portion 34 may be formed so that both the faces are continuous in the form of a substantially flat surface as shown in FIG. 3 to FIG. 4B, or may be formed so that both the faces are continuous with each other at an angle, though not shown.

A peripheral length of an outer periphery of the second grasping portion 34 (a peripheral length in a periaxial direction of the longitudinal axis L) is formed to be shorter than a peripheral length of an outer periphery of the first grasping portion 32. In particular, a peripheral length of an outer periphery of the first grasping portion 32 at a position close to the second grasping portion 34 (a peripheral length in the periaxial direction of the longitudinal axis L) is formed to be longer than the peripheral length of the outer periphery of the first grasping portion 32. A peripheral length of an outer periphery of the first grasping portion 32 at a position away from the second grasping portion 34 (a peripheral length in the periaxial direction of the longitudinal axis L) may be formed to be longer or shorter than the peripheral length of the outer periphery of the first grasping portion 32.

An inclined surface 82 inclined to the longitudinal axis L is formed between the third surface 56 of the first grasping portion 32 and the second grasping portion 34, specifically between an edge portion 56a of the third surface 56 of the first grasping portion 32 which is close to the second grasping portion 34 and the sixth surface (the grip face) 64 of the second grasping portion 34. In other words, the inclined surface 82 is formed to be inclined toward the insertion section 12 on an insertion section 12 side of the projecting portion 60. In particular, the inclined surface 82 is preferably formed on a side opposite to the fifth surface 62 of the second grasping portion 34.

The inclined surface 82 is orthogonal to a virtual line (a perpendicular line) T extended outside in the radial direction from the rotation central axis C toward a boundary between the third surface 56 and the sixth surface. In other words, the perpendicular line T of a certain position of the inclined surface 82 intersects the rotation central axis C of the UD bending operation knob 36. The inclined surface 82 may be formed as a flat surface or a curved surface. In a case where the inclined surface is formed as the curved surface, the inclined surface is preferably formed to be smoothly continuous with the third surface 56 of the first grasping portion 32 and the sixth surface 64 of the second grasping portion 34. Additionally, the inclined surface 82 is preferably positioned more distant from the rotation central axis C than the convex portion 72 as a circumscribed surface that comes in contact with a virtual circle CK based on the rotation central axis C of the UD bending operation knob 36.

A position of the first pressing valve unit 40 which is distant from the third surface 56 and close to the second grasping portion 34, i.e., a pressing member 40a is disposed at a position that comes in contact with a virtual surface VS parallel to the inclined surface 82. In a case where the first pressing valve unit 40 substantially having the same size and the same shape as in the second pressing valve unit 42 is used or the first pressing valve unit substantially having the same size and the same shape as in a conventional pressing valve unit is used, the position of the first pressing valve unit 40 to the edge portion 56a of the third surface 56 of the first grasping portion 32 changes in accordance with an inclination angle of the inclined surface 82. The inclined surface 82 is formed, thereby the position of the first pressing valve unit 40 is preferably closer to the edge portion 56a of the third surface 56 of the first grasping portion 32 shown in FIG. 3 than to a position corresponding to an edge portion of a third surface of a first grasping portion of an operation device of a conventional endoscope.

It is to be noted that in this embodiment, there will be described a case where the bending portion 24 is bent in a U-direction and a D-direction, i.e., a case where the UD bending operation knob denoted with reference sign 36 is operated. However, the RL bending operation knob 38 is suitably disposed at a position away from the second surface 54 to bend the bending portion 24 in an R-direction and an L-direction, and the bending portion 24 is preferably formed to be bent in the R-direction or the L-direction by an operation of the RL bending operation knob 38.

Next, an operation of the endoscope 10 according to this embodiment will be described with reference to FIG. 1 to FIG. 4B.

In a state where the first surface 52 of the first grasping portion 32 and the user facing surface (the fifth surface) 62 of the second grasping portion 34 are disposed to confront the user, the lower surface 44a of the connector 44 is disposed and supported on an index finger IF of the user's left hand, and a lower surface of the universal cord 16 is supported in the vicinity of a root of a thumb TH. The thumb TH is placed from the first surface 52 to the second surface 54 through a lower side of the universal cord 16. At this time, the thumb TH can be placed in the vicinity of a switch 46d of the switch unit 46 disposed at a position close to the user or the convex portion 72 of the UD bending operation knob 36. Conversely, as shown in FIG. 4A and FIG. 4B, the index finger IF is placed at a position where the pressing member 40a of the first pressing valve unit 40 is operable, or placed at a position where a pressing member 42a of the second pressing valve unit 42 is operable. A middle finger MF is placed at the position where the pressing member 40a of the first pressing valve unit 40 is operable, or placed at a position where the UD bending operation knob 36 is supportable.

It is to be noted that a thenar of the thumb TH in the palm of the user's left hand is placed in the vicinities of the first surface 52 and the fourth surface 58 and on left side faces of the fifth surface 62 and the sixth surface 64. In such states, the user grips the operation device 14 including the first and second grasping portions 32 and 34 with the left hand.

For the operation device of a conventional endoscope, in the first grasping portion and a second grasping portion, there is a stepped portion especially in a boundary between the third surface of the first grasping portion and a sixth surface of the second grasping portion, and peripheral lengths of the first grasping portion and the second grasping portion to a longitudinal axis rapidly change due to the stepped portion. Conversely, in the operation device 14 of the endoscope 10 according to this embodiment, the peripheral lengths of the periaxial direction of the longitudinal axis L around a boundary between the first grasping portion 32 and the second grasping portion 34 are gradually changed along the longitudinal axis L due to the presence of the inclined surface 82 orthogonal to the perpendicular line T directed out from the rotation central axis C in the radial direction.

Consequently, as in the state shown in, for example, FIG. 4A, the user can adjust a grasping position of the operation device 14 including the inclined surface 82 to a position in which the operation device is suitably easy to hold in accordance with, for example, a hand size or a portion to be fitted into the hand. For example, a user who has comparatively large hands preferably attaches, for example, the middle finger MF of the hand to an upper side of the inclined surface 82 (a position close to the third surface 56 of the first grasping portion 32 and away from the insertion section 12), because the peripheral length of the upper side of the inclined surface 82 in the periaxial direction of the longitudinal axis L is longer than that of a lower side of the inclined surface. Conversely, a user who has comparatively small hands preferably attaches, for example, the middle finger MF of the hand to the lower side of the inclined surface 82 (a position close to the sixth surface 64 of the second grasping portion 34 on the side opposite to the fifth surface 62, and close to the insertion section 12), because the peripheral length of the lower side of the inclined surface 82 in the periaxial direction of the longitudinal axis L is shorter than that of the upper side of the inclined surface.

In this state, the user holds the insertion section 12 with the right hand, and pushes the distal hard portion 22 of the insertion section 12 into a bore such as a body cavity to insert the tubular member 26 from the distal hard portion 22 of the insertion section 12.

For example, when the insertion section 12 is inserted into the bore of a large intestine or the like from an anus side toward a distal side, for example, a transverse colon or the like, the bending portion 24 is suitably bent in the U-direction and the D-direction. At this time, the user repeats an operation of turning the insertion section 12 grasped with the right hand in the periaxial direction of the longitudinal axis L or turning the UD bending operation knob 36 of the operation device 14 grasped with the left hand in a suitable direction to insert the insertion section 12 from a proximal side toward the distal side. When the bent state of the bending portion 24 is suitably held, the user holds the UD bending operation knob 36 not only with the thumb TH but also with, for example, the middle finger MF, a ring finger RF or the like.

When the bent state of the bending portion 24 is suitably held, i.e., when the UD bending operation knob 36 is held to maintain its position, the UD bending operation knob 36 is held with the middle finger MF or the ring finger RF while maintaining a state where the UD bending operation knob 36 is turned as much as a suitable amount with, for example, the thumb TH. Afterward, the thumb TH is released from the UD bending operation knob 36. At this time, in a case where the UD bending operation knob 36 is further turned, the knob may be turned with the middle finger MF, the ring finger RF or the like, or may be turned with the thumb TH.

In a case where the UD bending operation knob 36 is held with the middle finger MF, the middle finger MF is moved from, for example, a state where the middle finger MF is placed on the pressing member 40a of the first pressing valve unit 40 as shown in FIG. 4B to the UD bending operation knob 36 as shown in FIG. 4A. At this time, the middle finger MF is moved to the inclined surface 82 through the virtual surface VS while moving the ring finger RF and a little finger LF away from the inclined surface 82. At this time, the inclined surface 82 is positioned closer to the rotation central axis C than the virtual surface VS. Additionally, in this embodiment, a space between the edge portion 56a of the third surface 56 and the first pressing valve unit 40 is minimized. Consequently, it is hard for the middle finger MF to be stuck on the edge portion 56a of the third surface 56, and even if the middle finger MF is slightly stuck on the edge portion 56a, the middle finger MF is easily moved to a position shown in FIG. 4A, because the inclined surface 82 is continuous with the edge portion 56a. Further, the middle finger MF abuts on the suitable position of the inclined surface 82, whereby the UD bending operation knob 36 can be stably held with the middle finger MF.

In a case where the UD bending operation knob 36 is held with the ring finger RF, for example, the middle finger MF is moved from the position shown in FIG. 4A to a position shown in FIG. 4B, and the ring finger RF and the little finger LF are moved from positions shown in FIG. 4A to positions shown in FIG. 4B. When the middle finger MF is moved, the middle finger may be moved to the pressing member 40a along the inclined surface 82, the edge portion 56a of the third surface 56 and further, the first pressing valve unit 40. That is, the middle finger MF may gradually be moved to the pressing member 40a on a distant side along the inclined surface 82, the edge portion 56a of the third surface 56 and further, the first pressing valve unit 40 to the longitudinal axis L. At this time, during fingering of the middle finger MF, the finger is not stuck on anything. Additionally, a stepped portion between the edge portion 56a of the third surface 56 and the first pressing valve unit 40 according to this embodiment is also minimized. Therefore, the fingering of the middle finger MF from the position shown in FIG. 4A to the position shown in FIG. 4B can easily be performed. On the other hand, the ring finger RF and the little finger LF may be moved from the positions shown in FIG. 4A to the positions shown in FIG. 4B on a first grasping portion 32 side. Further, the ring finger RF abuts on a suitable position of the inclined surface 82, whereby the UD bending operation knob 36 can be stably held with the ring finger RF without unstably moving the ring finger RF.

As described above, the endoscope 10 according to this embodiment can be considered as follows.

Differently from the operation device of the conventional endoscope, in the operation device 14 of the endoscope 10 according to this embodiment, the inclined surface 82 is formed in the boundary between the first grasping portion 32 and the second grasping portion 34, and no steep stepped portions are formed. Consequently, during movement along an axial direction of the longitudinal axis L and movement in the peripheral direction of the longitudinal axis L, the middle finger MF, the ring, finger RF or the like can be prevented from being stuck on the stepped portion, and the movement of the middle finger MF or the ring finger RF can be prevented from being obstructed. Thus, the operation device 14 of the endoscope 10 according to this embodiment has the inclined surface 82, so that it is possible to smoothly perform both the movement of the middle finger MF or the ring finger RF along the axial direction of the longitudinal axis L and the movement of the finger along the peripheral direction around the longitudinal axis L. Therefore, for example, in a case where the UD bending operation knob 36 is supported with the middle finger MF or the ring finger RF, the middle finger MF or the ring finger RF can be prevented from being stuck on a part of the operation device 14 when the middle finger MF or the ring finger RF is moved along the inclined surface 82. Consequently, the user can perform an operation in a state where stress is decreased, when performing the operation of supporting the UD bending operation knob 36 with the middle finger MF or the ring finger RF.

Additionally, the operation device 14 according to this embodiment may be moved substantially linearly in a case where, for example, the middle finger MF is moved from the state shown in FIG. 4A to the state shown in FIG. 4B. Consequently, in the operation device 14 according to this embodiment, when a grasping state is changed by suitably moving the hand to the operation device 14, directions to move the finger can be minimized, and the fingering or the like can be simplified. Additionally, when, for example, the middle finger MF is placed on the pressing member 40a of the first pressing valve unit 40, the inclined surface 82 is parallel to an edge portion of the pressing member 40a of the first pressing valve unit 40. Consequently, when the user moves the middle finger MF from the inclined surface 82 to the pressing member 40a of the first pressing valve unit 40 or the user moves the middle finger MF from the pressing member 40a to the inclined surface 82, it is easy to perceive the position and move the finger to the position without visual confirmation.

According to this embodiment, the inclined surface 82 orthogonal to the rotation central axis C is formed between the first grasping portion 32 and the second grasping portion 34, and hence the first and second grasping portions 32 and 34 are easy to stably be grasped irrespective of the hand side, when grasping the grasping portions. Additionally, the peripheral lengths of the first and second grasping portions 32 and 34 to the longitudinal axis L are gradually changed along the longitudinal axis L by the inclined surface 82, and hence it is possible to improve, for example, an operability when the UD bending operation knob 36 is held with the middle finger MF or the like, an operability when the middle finger MF is moved from the position where the UD bending operation knob 36 is held to the pressing member 40a of the first pressing valve unit 40, and further, an operability when the middle finger MF attached to the pressing member 40a of the first pressing valve unit 40 is moved to hold the UD bending operation knob 36 with the middle finger MF or the like.

Therefore, according to this embodiment, there can be provided the operation device 14 of the endoscope 10 which is easy to stably be grasped and easy to be operated even in a case where the grasping state is changed by suitably moving a hand.

It is to be noted that according to the endoscope 10 of this embodiment, a shape of a large part of the operation device 14 and a diameter of the UD bending operation knob 36 are not changed, and a usual operation feeling can be maintained to the extent possible for a user who has heretofore used the endoscope.

In this embodiment, an example of the endoscope 10 has been described. Although not shown, it is also preferable to form an into-bore introduction device in which the illumination optical system and the observation optical system are removed from the endoscope 10.

Next, a second embodiment will be described with reference to FIG. 5. This embodiment is a modification of the first embodiment, the same members or members having the same functions as in the members described in the first embodiment are denoted with the same signs wherever possible, and detailed descriptions thereof are omitted.

Figure 5:
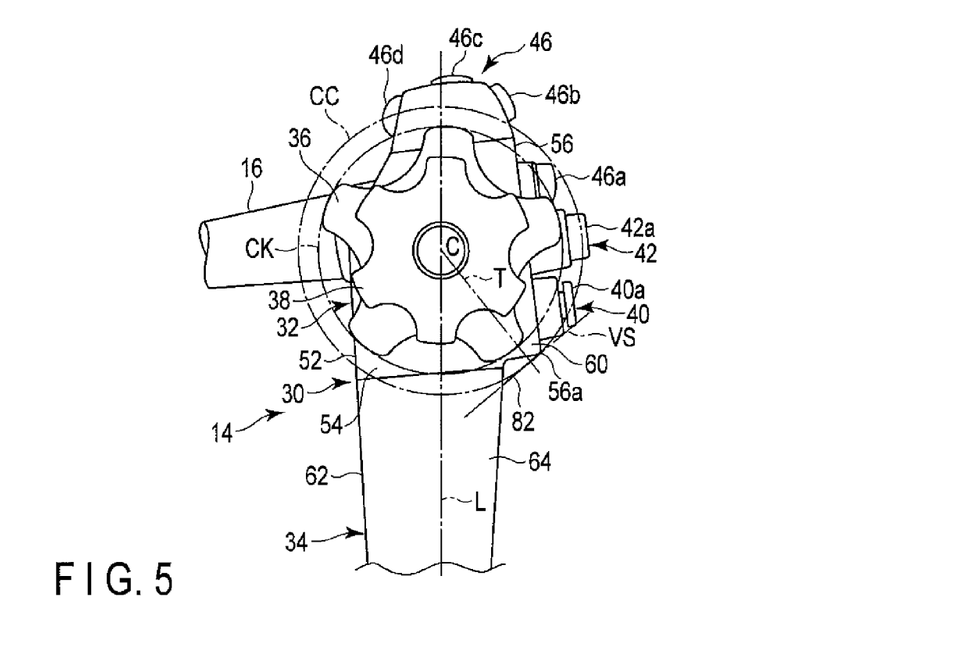
FIG. 5 is a schematic front view showing an operation device of the endoscope (the into-bore introduction device) according to the second embodiment.

As shown in FIG. 5, first and second pressing valve units 40 and 42 according to this embodiment have sizes different from each other. It is to be noted that the first and second pressing valve units 40 and 42 may have similarity shapes or different shapes.

Also when the embodiment is formed in this manner, an operation device 14 can be grasped and operated in the same manner as described in the first embodiment.

Further, the first pressing valve unit 40 and the second pressing valve unit 42 are formed into a size along a circle of a virtual circumscribed circle CC based on a rotation central axis C. Consequently, when fingers are moved, pressing members 40a and 42a of the first and second pressing valve units 40 and 42 can be operated by moving the fingers along the circle of the virtual circumscribed circle CC, and hence the members can easily be operated.

Next, a third embodiment will be described with reference to FIG. 6 and FIG. 7. This embodiment is a modification of the first and second embodiments, the same members or members having the same functions as in the members described in the first and second embodiments are denoted with the same signs wherever possible, and detailed descriptions thereof are omitted.

Figure 6:
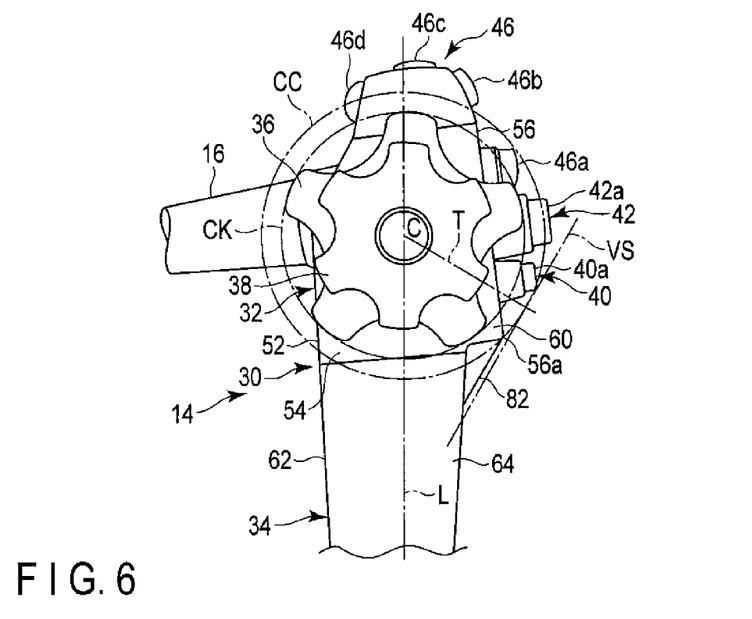
FIG. 6 is a schematic front view showing an operation device of the endoscope (the into-bore introduction device) according to the third embodiment.
Figure 7:
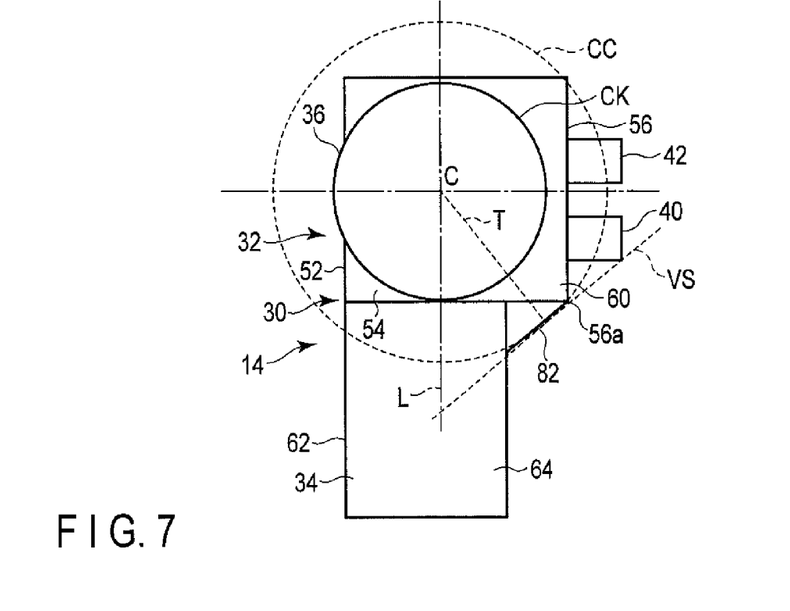
FIG. 7 is a schematic view showing the operation device of the endoscope (the into-bore introduction device) according to the third embodiment.

As shown in FIG. 6 and FIG. 7, an inclined surface 82 formed from an edge portion 56a of a lower end of a third surface 56 toward a sixth surface 64 of a second grasping portion 34 is orthogonal to a virtual line T. Further, in this embodiment, when it is supposed that there is a virtual circumscribed circle CC passing the edge portion 56a of the lower end of the third surface 56 based on a rotation central axis C of a UD bending operation knob 36, a position of a first pressing valve unit 40 which is distant from the third surface 56 and close to the second grasping portion 34 is disposed on an extended line of a virtual parallel surface VS that is parallel to the inclined surface 82 and comes in contact with the circumscribed circle CC.

Also, when the embodiment is formed in this manner, an operation device 14 can be grasped and operated in the same manner as described in the first embodiment. Further, as described in the second embodiment, when fingers are moved, pressing members 40a and 42a of the first pressing valve unit 40 and a second pressing valve unit 42 can be operated by moving the fingers along a circle of the virtual circumscribed circle CC, and hence the members can easily be operated.

In the abovementioned first to third embodiments, there has been described the case where the position of the pressing valve unit 40 which is distant from the third surface 56 and close to the second grasping portion 34 is disposed at the position that comes in contact with the virtual surface VS parallel to the inclined surface 82. Needless to say, this virtual line is preferably present on the extended line of the inclined surface 82. That is, the position of the pressing valve unit 40 which is distant from the third surface 56 and close to the second grasping portion 34 is also preferably disposed at the position that comes in contact with the virtual extended line VS of the inclined surface 82.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation device for an into-bore introduction device, comprising:

a grasping section that is connected to a proximal portion of an insertion section to be inserted into a bore, and is to be grasped by an operator to operate the insertion section, the grasping section includes a first grasping portion, and a second grasping portion that is disposed on a side closer to the insertion section than the first grasping portion;

a bending operation knob that is disposed on the grasping section and that bends a bending portion of the insertion section;

a projecting portion that is formed to project from the grasping section in a direction radial to a longitudinal axis of the grasping section, in a third surface between a second surface on which the bending operation knob is disposed and a fourth surface; and an inclined surface that is formed to be orthogonal to a virtual line extended out from a rotation central axis of the bending operation knob in a radial direction toward a boundary between the third surface of the projecting portion on which a pressing valve unit is disposed and a grip face of the grasping section which is formed closer to the insertion section than the projecting portion, and which is formed to be inclined to the longitudinal axis, wherein:

a distal end of the pressing valve unit is disposed at a position that comes into contact with a virtual surface parallel to the inclined surface, and the virtual surface is positioned at the insertion section side.

2. The operation device according to claim 1, wherein the grasping section includes:

the first grasping portion that includes a first surface, the second surface, the third surface, and the fourth surface to form an annular shape; and the second grasping portion that includes a fifth surface disposed continuously with the first surface, and a sixth surface disposed in the peripheral direction of the longitudinal axis and cooperating with the fifth surface to form the annular shape in the direction peripheral to the longitudinal axis.

3. The operation device according to claim 2, wherein the bending operation knob is disposed on the second surface of the first grasping portion, the second surface being adjacent to the first surface and the third surface opposite to the first surface, the second surface being opposite to the fourth surface, and the bending operation knob having a rotation central axis.

4. The operation device according to claim 3, wherein in the first grasping portion, the pressing valve unit is disposed on the third surface adjacent to the second surface and the fourth surface and opposite to the first surface, and positioned more distant from the longitudinal axis than the sixth surface at the position close to at least the second grasping portion.

5. The operation device according to claim 2, wherein a position of the pressing valve unit which is distant from the third surface and close to the second grasping portion is disposed at a position that comes in contact with a virtual extended line of the inclined surface.

6. The operation device according to claim 1, wherein the inclined surface is positioned more distant from the rotation central axis than a circumscribed surface that comes in contact with a virtual circle based on the rotation central axis of the bending operation knob.

7. An into-bore introduction device comprising:

the operation device for the into-bore introduction device according to claim 1; and an insertion section that is extended to the grasping section along the longitudinal axis, and that includes a bending portion.

* * * * *